United States Patent

Dolfini

[11] 3,989,697
[45] *Nov. 2, 1976

[54] 7-METHOXY PHENYLUREIDOCEPHALOSPORINS

[75] Inventor: Joseph Edward Dolfini, Princeton, N.J.

[73] Assignee: E. R. Squibb & Sons, Inc., Princeton, N.J.

[*] Notice: The portion of the term of this patent subsequent to Nov. 2, 1993, has been disclaimed.

[22] Filed: May 2, 1973

[21] Appl. No.: 356,678

[52] U.S. Cl. ............................ 260/243 C; 424/246
[51] Int. Cl.² ........................................ C07D 501/54
[58] Field of Search ............................ 260/243 C

[56] References Cited
UNITED STATES PATENTS

| | | | |
|---|---|---|---|
| 3,673,183 | 6/1972 | Erickson | 260/243 C |
| 3,708,479 | 1/1973 | Welch et al. | 260/243 C |
| 3,778,432 | 12/1973 | Pines | 260/243 C |
| 3,780,031 | 12/1973 | Christensen et al. | 260/243 C |
| 3,780,033 | 12/1973 | Hazen | 260/243 C |
| 3,780,033 | 12/1973 | Hazen | 260/243 C |
| 3,780,034 | 12/1973 | Christensen et al. | 260/243 C |
| 3,780,037 | 12/1973 | Hazen | 260/243 C |
| 3,843,641 | 10/1974 | Christensen | 260/243 C |
| 3,860,591 | 1/1975 | Breuer | 260/243 C |
| 3,867,380 | 2/1975 | Dunn et al. | 260/243 C |

Primary Examiner—Paul M. Coughlan, Jr.
Attorney, Agent, or Firm—Lawrence S. Levinson; Merle J. Smith; Stephen B. Davis

[57] ABSTRACT

Compound of the formula

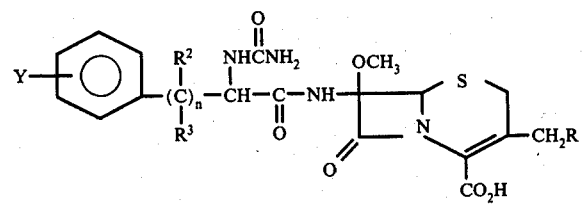

wherein Y is H, lower alkyl, lower alkoxy, halogen, $CF_3$, nitro or hydroxy, $R^2$ and $R^3$ each are H or lower alkyl, n is 0–3 and R is H or

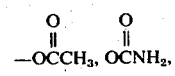

pyridinium or S-heterocyclic, and pharmaceutically acceptable salts and esters thereof are effective antibacterial agents. In general the preferred products are those wherein the methoxy group is designated the α-configuration.

8 Claims, No Drawings

7-METHOXY PHENYLUREIDOCEPHALOSPORINS

BACKGROUND OF THE INVENTION

Derivatives of 6-aminopenicillanic acid and of 7-aminocephalosporanic acid are known and have been described as antibacterial agents. There is, however, a continuing need for new antibacterial agents which are effective against additional gram-positive and gram-negative organisms, are effective against resistant organisms or which may be utilized when bacteria develop resistance to known antibacterial agents, or which are particularly effective against certain hard to control organisms.

SUMMARY OF THE INVENTION

This invention relates to new 7-methoxy phenylureidocephalosporins of the general formula

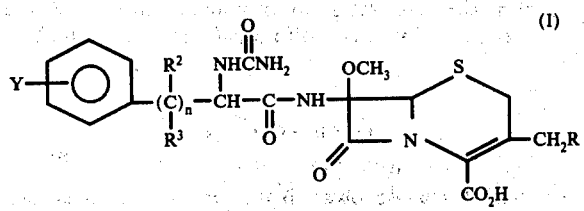

wherein Y is hydrogen or alkyl or alkoxy each of 1 to 4 carbons, halogen (F, Cl, Br or I), $CF_3$, nitro or hydroxy, $R^2$ and $R^3$ each are H or alkyl of 1 to 4 carbons, $n$ is 0, 1, 2 or 3, and R is H,

pyridinyl-1-oxo-2-thio; 3-methyl-1,2,4-thiadiazolylthio; 1-methyltetrazolyl-5-thio; 2-methyl-1,3,4-thiadiazolyl-5-thio;

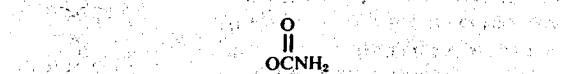

or pyridinium and to pharmaceutically acceptable carboxylate salts, lower alkyl esters, or acyloxymethyl esters thereof. The compounds of the present invention are effective antibacterial agents and are useful in the treatment of many gram negative and gram positive infections. These compounds are useful as disinfectants and also as nutritional supplements in animal feeds. The 7-methoxy group occupies the α-configuration.

DETAILED DESCRIPTION

The compounds of the present invention may be prepared by coupling an activated form of a phenyl-α-aminoalkanoic acid of the formula

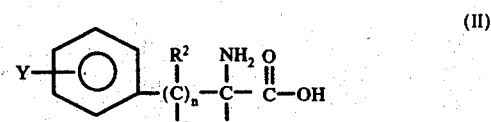

wherein Y, $n$, $R^2$, $R^3$ and H are as defined above with a protected ester of 7-amino-7-methoxycephalosporanic acid (7-AMCA) or of 7-amino-7-methoxy-3-desacetoxycephalosporanic acid (7-AMDCA), and then reacting that product with an alkali metal cyanate or an alkaline earth metal cyanate to yield the compound of formula I. For the purpose of the invention, the 7-AMCA or 7-AMDCA compound chosen is that with the α-configuration of the 7-methoxy group.

Alternatively, a compound of formula II, produced by any suitable method can be reacted with an alkali metal cyanate or an alkaline earth metal cyanate to form an α-ureido compound of the formula

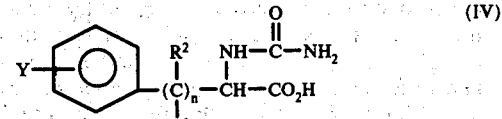

This reaction takes place by treating an aqueous suspension of the α-amino acid with the alkali or alkaline earth metal cyanate. Acidification with hydrochloric acid precipitates the α-ureido acid in good yield. A solution of the α-ureido acid in an organic solvent containing a tri-(lower)alkyl amine is converted to a mixed carbonic or other anhydride by treating with an anhydride forming reagent, e.g., a lower alkyl chloroformate, an aryl chloroformate, or an acyl halide, at reduced temperatures of from about 0° to about −20° C.

Reaction at reduced temperatures of the mixed anhydride with a protected ester of 7-amino-7-methoxycephalosporanic acid (7-AMCA) or a protected ester of 7-amino-7-methoxy-3-desacetoxy-cephalosporanic acid (7-AMDCA) or a protected ester of a compound of formula V

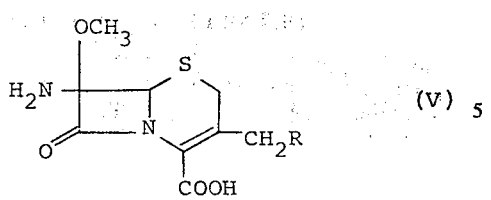

yields the compounds I of the present invention wherein R is acetoxy, H, or carbamoyloxy respectively, after removal of the ester protecting group.

Alternatively, a compound of formula I may be obtained by converting a compound of formula IV to an activated ester or by reacting a compound of formula IV with a carboxyl group activating agent, such as, for example, dicyclohexylcarbodiimide or bisimidazole carbonyl, and then coupling the activated form of the compound of formula IV with a protected ester of 7-AMCA or a protected ester of 7-AMDCA. In some cases, as will be obvious to those skilled in the art, the carboxyl group may be activated by conversion to an acid halide, e.g., the chloride, or to an azide prior to coupling with a protected ester of 7-AMCA or a protected ester of 7-AMDCA. A more detailed discussion of carboxyl activating groups may be obtained by reference to standard works on peptide synthesis, for example, Bodanszky et al., "Peptide Synthesis", Interscience, 1966.

Alternatively, the α-amino acid of formula II may be used to acylate a protected ester of 7-AMCA or a protected ester of 7-AMDCA. The resulting α-amino acid derivative of a protected ester of 7-AMCA or a protected ester of 7-AMDCA is then reacted with an alkali metal cyanate or an alkaline earth metal cyanate in the presence of water and the ester group removed to form the compounds I of the present invention.

The α-amino acid (II) or the α-ureido acid IV obtained occurs as a racemate of d and l optical isomers. It is generally possible to resolve these compounds by using optically pure bases (or acids) using methods known to the art, for example, as described by L. Velluz, "Substances Naturelle de Synthesese," 9, pp. 119–174 (1954), or E. L. Eliel, "Stereochemistry of Carbon Compounds," Chapter 4, McGraw-Hill Book Co., N.Y. (1962). The resulting pure d or l acid may then be coupled to the 7-AMCA or 7-AMDCA moiety. Generally the coupling of the d form leads to the more active product.

When preparing compounds of the present invention according to the reaction sequence wherein an α-amino acid is acylated with a protected ester of 7-AMCA or a protected ester of 7-AMDCA, it may be desirable to protect the α-amino group during the acylation reaction by means of an amino protecting group. Such amino protecting groups are well known in the art and are described, for example, by Bodanszky et al., "Peptide Synthesis," supra.

Specific examples of methods for acylating the protected ester of 7-AMCA or a protected ester of 7-AMDCA are similar to those described for the acylation of 7-ACA or 7-ADCA, for example, in Netherlands Pat. No. 6,812,382, Belgian Pat. No. 675,298, as well as in the following articles:

Spencer et al., J. Med. Chem., 9, 746 (1966);
Ryan et al., ibid. 12, 310 (1969).

Compounds of formula V wherein R is heterocyclylthio or pyridinium may be obtained from an acylated 7-AMCA by methods known in the art for the formation of 7-aminocephalosporanic acid analogs, e.g., Abraham and Newton (1950) Ciba Foundation Symposium, Amino Acids, Peptides, Antimetabolic Activity, p. 205; U.S. Pat. No. 3,225,038; and Belgian Pat. Nos. 641,338 and 652,148.

The carboxylate salts of the compounds (I) of the present invention are formed by reacting the carboxyl group of the 7-AMCA or 7-AMDCA moiety with a salt-forming ion, e.g., an alkali metal such as sodium or potassium, or an alkaline earth metal such as magnesium or calcium or a metal of group IIIA such as aluminum, or the radical of an organic base such as dibenzylamine, N,N'-dibenzylethylenediamine or other organic bases known to form salts with cephalosporanic acids.

The lower alkyl esters may be obtained by esterifying the carboxyl group of the 7-AMCA or 7-AMDCA moiety with a straight or branched chain lower alkyl halide of from 1 to 3 carbon atoms, e.g., methyl chloride, ethyl bromide and the like, or with a diazoalkane of from 1 to 3 carbon atoms, e.g., diazomethane, diazoethane, and the like. The resulting ester group is then formed by a radical such as methyl, ethyl, propyl or isopropyl.

The acyloxymethyl esters may be obtained according to known methods, for example a method adapted from that of Daehne et al., J. Med. Chem. 13, 607 (1970), by reacting the carboxyl group or a metal salt thereof of a compound of formula I with a halide of the formula

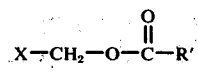

wherein R' may be lower alkyl of up to 5 carbon atoms, phenyl, benzyl or phenethyl, and X is chlorine or bromine. Thus, suitable compounds include acetoxymethyl chloride, propionyloxymethyl chloride, butyryloxymethyl chloride, pivaloyloxymethyl chloride, valeryloxymethyl chloride, benzoyloxymethyl chloride, or phenacetoxymethyl chloride, and the like.

It will be appreciated that certain of the compounds of this invention exist in various states of solvation as well as in different optically active forms. The various forms as well as their mixtures are within the scope of this invention.

The compounds of this invention have a broad spectrum of antibacterial activity against both gram positive and gram negative organisms such as *Staphylococcus aureus, Salmonella schottmuelleri, Proteus vulgaris, Escherichia coli* and *Streptococcus pyogenes*. They may be used as antibacterial agents in a prophylactic manner, e.g., in cleaning or disinfecting compositions, or otherwise to combat infections due to organisms such as those named above, and in general may be utilized in a manner similar to cephalosporin C, cephalothin and other cephalosporins. For example, a compound of formula I or a physiologically acceptable salt or ester thereof may be used in various animal species in an amount of about 1 to 200 mg./kg. daily, orally or parenterally, in single or two to four divided doses to treat infections of bacterial origin.

Up to about 600 mg. of a compound of formula I or a pharmaceutically acceptable salt or ester thereof may be incorporated in an oral dosage form such as tablets, capsules or elixirs or in an injectable form in a sterile aqueous vehicle prepared according to conventional pharmaceutical practice.

In cleaning or disinfecting compositions, e.g., in barns or dairy equipment, a concentration of about 0.01 to 1% by weight of such compounds admixed with, suspended or dissolved in conventional inert dry or aqueous carriers for application by washing or spraying may be used.

They are also useful as nutritional supplements in animal feeds.

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The 7-AMCA or 7-AMDCA compound or the compound of formula V selected for the coupling reactions in the following examples are chosen with the 7-α-methoxy configuration.

The following examples illustrate the present invention without, however, limiting the same thereto. All temperatures are on the centigrade scale.

EXAMPLE 1

7-[2-Ureido-2-(phenyl)acetamido]-7-methoxycephalosporanic acid

A suspension of D-2-amino-2-(phenyl)acetic acid (0.10 moles) in 150 ml. of water is treated with 8.1 g. of potassium cyanate. The resulting mixture is heated to about 80° C to give a clear solution which is then allowed to stand at room temperature for about 24 hours. Acidification to pH 3.5–5 with hydrochloric acid precipitates the α-ureido compound. A solution containing 0.10 moles of the α-ureido acid in 100 ml. of acetone containing 10.1 g of triethylamine at a temperature of from about 0° C to about −20° C is converted to a mixed carbonic anhydride by treating with 10.8 g of ethyl chloroformate for about 30 minutes. A cold (about −10° C) solution of 0.1 Mol of 7-amino-7-methoxycephalosporanic acid benzhydryl ester in 400 ml of acetone containing 10.1 g of triethylamine is added to the solution of mixed anhydride and the reaction mixture stirred vigorously at about 0° C for approximately 30–45 minutes. The volume of the solution is reduced by evaporating the bulk of the acetone at reduced pressure at room temperature or below. One liter of ethyl acetate is added and the solution washed with 2 × 200 ml of ice cold 5% aqueous sodium bicarbonate, 100 ml of water, 2 × 200 ml of 0.5 molar hydrochloric acid, and 100 ml again of water. The ethyl acetate solution is dried ($Na_2SO_4$) and evaporated to deposit the benzhydryl ester of the title compound.

The free acid is obtained by dissolving the ester (1 g) and anisole (500 mg) in 20 ml of ice cold trifluoroacetic acid and keeping it at 0°–5° C for 30 minutes. The acid solvent is evaporated at reduced pressure. The residue is treated with 50 ml of water and the pH adjusted to 7.5 with sodium hydroxide to dissolve the product. The solution is washed with ethyl acetate. (Lyophilization of the aqueous solution deposits the sodium salt of the title compound). The aqueous layer is acidified to precipitate the title compound.

EXAMPLE 2

7-[2-Ureido-2-(phenyl)acetamido]-7-methoxy-3-desacetoxycephalosporanic acid

Following the procedure of example 1 but substituting 0.1 mol of 7-amino-7-methoxy-3-desacetoxycephalosporanic acid benzhydryl ester for 7-amino-7-methoxycephalosporanic acid ester, the title compound is obtained.

EXAMPLE 3

Pivaloyloxymethyl ester of 7-[2-ureido-(phenyl)acetamido]-7-methoxy-cephalosporanic acid Chloromethylpivalate (20 mmole) is combined with 10 mmole of the product of example 1, 0.4 ml. of a 5% aqueous sodium iodide solution, and 170 ml. of acetone. Triethylamine, 2.0 gm. (20 mmole), is added and the mixture stirred for 10 hours, then refluxed for 1 hour. The reaction mixture is cooled and concentrated in vacuo. The residue is partitioned between ethyl acetate, and 5% aqueous sodium bicarbonate. The organic layer is dried over sodium sulfate and evaporated to give the crude product which is obtained as a powder upon trituration with ether.

EXAMPLE 4

Acetoxymethyl ester of 7-[2-ureido-2-(phenyl)acetamido]-7-methoxycephalosporanic acid Following the procedure of example 3 but substituting 20 mmole of the chloromethylacetate for the chloromethylpivalate, the title compound is obtained.

EXAMPLE 5

7-[2-Ureido-2-(phenyl)acetamido]-7-methoxy-3-desacetoxycephalosporanic acid, methyl ester A 0.1 molar solution of the product of example 2 in dimethoxyethane is treated with an excess of ethereal diazomethane. Evaporation of the solvent at reduced pressure deposits the title compound.

EXAMPLE 6

7-[2-Ureido-2-(phenyl)acetamido]-7-methoxycephalosporanic acid, ethyl ester

Following the procedure of example 5 but substituting the product of example 1 for the product of example 2, and substituting diazoethane for diazomethane, the title compound is obtained.

EXAMPLE 7

7-[2-Ureido-2-(phenyl)acetamido]-7-methoxycephalosporanic acid, potassium salt

One millimole of the product of example 1 is dissolved in 10 ml. of a 0.1 N aqueous KOH solution. Lyophilization of the solution yields the title compound.

EXAMPLE 8

7-[2-Ureido-2-(phenyl)acetamido]-7-methoxy-3-desacetoxy-cephalosporanic acid, calcium salt One millimole of the product of example 2 is dissolved in 10 ml. of a 0.05 N aqueous Ca(OH)$_2$ solution. Lyophilization of the solution yields the title compound.

EXAMPLE 9

7-[2-Ureido-2-(phenyl)acetamido]-7-methoxycephalosporanic acid, N,N'-dibenzylethylenediamine salt A solution of 0.010 mol of the product of example 1 in 25 ml of ethanol is added to a solution of 1.20 g of N,N'-dibenzylethylenediamine in 25 ml of ethanol at room temperature. After 15 minutes stirring the solvent is evaporated to deposit the title compound.

EXAMPLE 10

7-[2-Ureido-2-(phenyl)acetamido]-7-methoxy-3-[2-(5-methyl-1,3,4-thiadiazolyl)-thiomethyl]-Δ$^3$-cephem-4-carboxylic acid A solution of (0.026 mole) of the product of example 1 NaHCO$_3$ (2.1 g) and 3.8 g 2-mercapto-5-methyl-1,3,4-thiadiazole in 200 ml of pH 6.4 phosphate buffer is stirred for 5.5 hours at 60° C. The reaction is cooled to room temperature, acidified to pH 3 and extracted with ethyl acetate. The ethyl acetate layer is worked with saturated NaCl solution, dried (Na$_2$SO$_4$) and evaporated at reduced pressure to deposit the product.

EXAMPLES 11–13

Following the procedure of example 10 but substituting for 2-mercapto-5-methyl-1,3,4-thiadiazole, the heterocyclylthio compound listed below in column I, there is obtained respectively the final compound of column II

| | I | II |
|---|---|---|
| 11. | Pyridinyl-1-oxo-2-thiol | 7-[2-Ureido-2-(phenyl)acetamido]-7-methoxy-3-[2-(1-oxopyridinyl)thiomethy Δ$^3$-cephem-4-carboxylic acid |
| 12. | 3-methyl-1,2,4-thiadiazolyl-5-thiol | 7-[2-Ureido-2-(phenyl)-acetamido]-7-methoxy-3-[5-(3-methyl-1,2,4-thiadiazolyl)thiomethyl]-Δ$^3$-cephem-4-carboxylic acid |
| 13. | 1-methyltetrazolyl-5-thiol | 7-[2-Ureido-2-(phenyl)-acetamido]-7- |

-continued

| | I | II |
|---|---|---|
| | | methoxy-3-[5-(1-methyltetrazolyl)thiomethyl]-Δ$^3$-cephem-4-carboxylic acid |

EXAMPLE 14

7-[2-Ureido-2-(phenyl)acetamido]-7-methoxy-3-carbamoyloxy-methyl-Δ$^3$-cephem-4-carboxylic acid A solution containing 0.10 moles of D-2-ureido-2-(phenyl)acetic acid in 100 ml of acetone containing 10.1 g of triethylamine at a temperature of from about 0° C to about −20° C is converted to a mixed carbonic anhydride by treating with 10.8 g of ethyl chloroformate for about 30 minutes. A cold (about −10° C) solution of 0.10 mol of 7-amino-7-methoxy-3-carbamoyloxy-methyl-Δ$^3$-cephem carboxylic acid, (prepared by the method indicated in Netherlands Pat. No. 7,204,982) in 400 ml of 1:1 acetone containing 10.1 g of triethylamine is added to the solution of mixed anhydride and the reaction mixture stirred vigorously at about 0° C for approximately 30–45 minutes. The volume of the solution is reduced by evaporating the bulk of the acetone at reduced pressure at room temperature or below.

One liter of ethyl acetate is added and the solution washed with 2 × 200 ml of ice cold 5% aqueous sodium bicarbonate, 100 ml of water, 2 × 200 ml of 0.5 molar hydrochloric acid, and 100 ml again of water. The ethyl acetate solution is dried (Na$_2$SO$_4$) and evaporated to deposit the benzhydryl ester of the title compound.

The free acid is obtained by dissolving the ester (1 g) and anisole (500 mg) in 20 ml of ice cold trifluoroacetic acid and keeping it at 0°–5° C for 30 minutes. The acid solvent is evaporated at reduced pressure. The residue is treated with 50 ml of water and the pH adjusted to 7.5 with NaOH to dissolve the product. The solution is washed with ethyl acetate. (Lyophilization of the aqueous solution deposits the sodium salt of the title compound). The aqueous layer is acidified to precipitate the title compound.

EXAMPLE 15

7-[2-Ureido-3-(phenyl)propionamido]-7-methoxycephalosporanic acid

Following the procedure of example 1 but substituting an equivalent amount of 3-(phenyl)propionic acid, the title compound is obtained.

EXAMPLE 16

7-[2-Ureido-3-(4-methoxyphenyl)propionamido]-7-methoxy-3-desacetoxycephalosporanic acid Following the procedure of example 2 but substituting 3-(4-methoxyphenyl)propionic acid for 3-(phenyl)-propionic acid, the title compound is obtained.

EXAMPLE 17

7-[2-Ureido-2-(phenyl)acetamido]-7-methoxycephalosporanic acid

A solution containing 0.10 moles of the α-ureido 2-(phenyl)acetic acid in 100 ml of acetone containing 10.1 g of triethylamine at a temperature of from about 0° C to about −20° C is converted to a mixed carbonic anhydride by treating with 10.8 g of ethyl chloroformate for about 30 minutes. A cold (about −10° C) solution of 0.10 mol of 7-amino-7-methoxy-3-cephalosporanic acid, trichloroethyl ester in 400 ml of 1:1 acetone containing 10.1 g of triethylamine is added to the solution of mixed anhydride and the reaction mixture stirred vigorously at about 0° C for approximately 30–45 minutes. The volume of the solution is reduced by evaporating the bulk of the acetone at reduced pressure at room temperature or below.

One liter of ethyl acetate is added and the solution washed with 2 × 200 ml of ice cold 5% aqueous sodium bicarbonate, 100 ml of water, 2 × 200 ml of 0.5 molar hydrochloric acid, and 100 ml again of water. The ethyl acetate solution is dried ($Na_2SO_4$) and evaporated to deposit the trichloroethyl ester of the title compound.

The free acid is obtained by dissolving the ester (1 g) in 30 ml of cold 90% acetic acid at 0°–5° C for 1 hour. The acid solvent is evaporated at reduced pressure. The residue is treated with 50 ml of water and the pH adjusted to 7.5 with NaOH to dissolve the product. The solution is washed with ethyl acetate. (Lyophilization of the aqueous solution deposits the sodium salt of the title compound). The aqueous layer is acidified to precipitate the title compound.

EXAMPLES 18–34

The substituted benzaldehyde listed below is converted to the corresponding α-amino acid by the Strecker amino acid synthesis, Ann, 75, 27 (1850); 91, 349 (1854) wherein the aldehyde is reacted simultaneously with ammonia and HCN followed by hydrolysis of the resulting aminonitrile. The amino acid so produced is then substituted for D-2-amino-2-(phenyl)acetic acid in following the procedure of example 1. The final product is a 7-[2-ureido-2-(substituted phenyl)acetamido]-7-methoxycephalosporanic acid wherein the phenyl substituent corresponds to that of the starting benzaldehyde.

18. o-chlorobenzaldehyde;
19. p-chlorobenzaldehyde;
20. p-fluorobenzaldehyde;
21. 2-hydroxybenzaldehyde (salicylaldehyde);
22. 3-hydroxybenzaldehyde;
23. 4-hydroxybenzaldehyde;
24. 2-methylbenzaldehyde (o-toluylaldehyde);
25. 3-methylbenzaldehyde (m-methylbenzaldehyde);
26. 4-methylbenzaldehyde (p-methylbenzaldehyde);
27. 2-methoxybenzaldehyde (o-anisaldehyde);
28. 3-methoxybenzaldehyde;
29. 4-methoxybenzaldehyde (p-anisaldehyde);
30. 4-butoxybenzaldehyde;
31. 3-trifluoromethylbenzaldehyde;

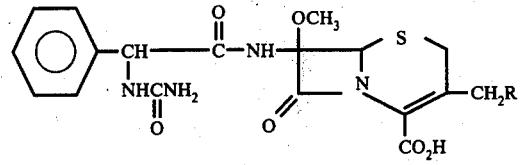

32. 3-iodobenzaldehyde;
33. 3-nitrobenzaldehyde;
34. 4-bromobenzaldehyde;

EXAMPLE 35

A sterile powder for reconstitution for use intramuscularly is prepared from the following ingredients which supply 1000 vials each containing 250 mg. of active ingredient:

| | |
|---|---|
| 7-[2-Ureido-2-(phenyl)acetamido]-7-methoxycephalosporanic acid, Na salt, sterile | 250 mg. |
| Lecithin powder, sterile | 50 gm. |
| Sodium carboxymethylcellulose, sterile | 20 gm. |

The sterile powders are aseptically blended, subdivided, filled into sterile vials and sealed. The addition of 1 ml. of water for injection to the vial provides a suspension for intramuscular injection.

EXAMPLE 36

Tablets are prepared from the following ingredients:

| | |
|---|---|
| 7-[2-Ureido-2-(phenyl)acetamido]-7-methoxycephalosporanic acid, pivaloyloxymethyl ester | 5 kg. |
| Polyvinyl pyrrolidone | 360 gm. |
| Lactose | 780 gm. |
| Talc | 80 gm. |
| Magnesium stearate | 80 gm. |

The active substance is mixed with the lactose and granulated with an ethanol solution of the polyvinyl pyrrolidone. The wet material is screened and admixed with the talc and magnesium stearate. The mixture is compressed in a tableting machine to obtain 10,000 tablets weighing a total of 630 mg. each and containing 500 mg. of active ingredient.

What is claimed is:
1. A compound of the formula:

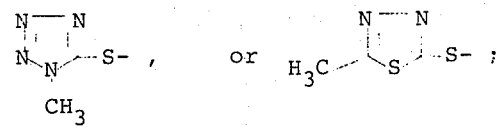

wherein the 7-methoxy group is in the α-configuration; R is

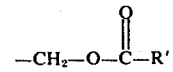

and a pharmaceutically acceptable salt thereof, a straight or branched chain alkyl ester of 1 to 3 carbon atoms thereof, or an acyloxymethyl ester thereof having the formula $$-CH_2-O-\overset{O}{\underset{\|}{C}}-R'$$

wherein R' is lower alkyl of 1 to 5 carbon atoms, phenyl, benzyl or phenethyl.

2. An acetoxymethyl ester of a compound of claim 1.

3. A pivaloyloxymethyl ester of a compound of claim 1.

4. A pharmaceutically acceptable salt of a compound of claim 1.

5. The compound of claim 1 as the free acid.

6. The compound of claim 5 wherein R is

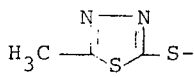

7. The compound of claim 5 wherein R is

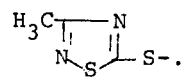

8. The compound of claim 5 wherein R is

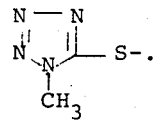

* * * * *

UNITED STATES PATENT AND TRADEMARK OFFICE
CERTIFICATE OF CORRECTION

PATENT NO. : 3,989,697
DATED : November 2, 1976
INVENTOR(S) : Joseph Edward Dolfini It is certified that error appears in the above—identified patent and that said Letters Patent are hereby corrected as shown below:

Example 11, col. II, "thiomethy" should read -- thiomethyl]- --.

Signed and Sealed this

Eleventh Day of January 1977

[SEAL]

Attest:

RUTH C. MASON
Attesting Officer

C. MARSHALL DANN
Commissioner of Patents and Trademarks